US011193943B2

(12) United States Patent
Goetzl

(10) Patent No.: US 11,193,943 B2
(45) Date of Patent: Dec. 7, 2021

(54) ENDOTHELIAL CELL DERIVED EXOSOMES AND USES THEREOF

(71) Applicant: Edward Goetzl, San Francisco, CA (US)

(72) Inventor: Edward Goetzl, San Francisco, CA (US)

( * ) Notice: Subject to any disclaimer, the term of this patent is extended or adjusted under 35 U.S.C. 154(b) by 0 days.

(21) Appl. No.: 15/703,955

(22) Filed: Sep. 13, 2017

(65) Prior Publication Data

US 2018/0224465 A1 Aug. 9, 2018

Related U.S. Application Data

(60) Provisional application No. 62/455,582, filed on Feb. 6, 2017.

(51) Int. Cl.
  *G01N 33/68* (2006.01)
  *G01N 33/573* (2006.01)
  *G01N 33/86* (2006.01)

(52) U.S. Cl.
  CPC ....... *G01N 33/6893* (2013.01); *G01N 33/573* (2013.01); *G01N 33/86* (2013.01); *G01N 2333/49* (2013.01); *G01N 2333/60* (2013.01); *G01N 2333/70503* (2013.01); *G01N 2333/70542* (2013.01); *G01N 2333/70596* (2013.01); *G01N 2333/755* (2013.01); *G01N 2333/90254* (2013.01); *G01N 2800/2871* (2013.01); *G01N 2800/32* (2013.01); *G01N 2800/52* (2013.01)

(58) Field of Classification Search
  CPC .. G01N 33/6893; G01N 33/573; G01N 33/86; G01N 2333/49; G01N 2333/60; G01N 2333/70503; G01N 2333/70542; G01N 2333/70596; G01N 2333/755; G01N 2333/90254; G01N 2800/2871; G01N 2800/32; G01N 2800/52; G01N 33/5064; G01N 33/5076; G01N 2030/8813; G01N 2333/475
  See application file for complete search history.

(56) References Cited

U.S. PATENT DOCUMENTS

2012/0295286 A1  11/2012  Berg

FOREIGN PATENT DOCUMENTS

| WO | WO 2009/015357 A1 | 1/2009 | |
| WO | WO 2012/115885 A1 | 8/2012 | |
| WO | WO-2012115885 A1 * | 8/2012 | ........... C12Q 1/6886 |

OTHER PUBLICATIONS

Ge and Wang. Identifying novel biomarkers for cardiovascular disease risk predication. J Intern Med 2012; 272: 430-439 (Year: 2012).*
Kernagis et al. Evolving Role of Biomarkers in Acute Cerebrovascular Disease. Ann Neurol 2012;71:289-303 (Year: 2012).*
Husseini and Laskowitz. Clinical application of blood biomarkers in cerebrovascular disease. Expert Review of Neurotherapeutics, 2010; 10(2):189-203 (Year: 2010).*
De Jong et al. Cellular stress conditions are reflected in the protein and RNA content of endothelial cell derived exosomes. Journal of Extracellular Vesicles 2012, 1:1, 18396 (Year: 2012).*
De Jong et al. Exosomes from hypoxic endothelial cells have increased collagen crosslinking activity through up-regulation of lysyl oxidase-like 2. J. Cell. Mol. Med. Vol 20, No. 2, 2016 pp. 342-350 (Year: 2015).*
Dignat-George and Boulanger. Arteriosclerosis, Thrombosis, and Vascular Biology. 2011;31:27-33 (Year: 2011).*
Suzuki E. et al. "Stem cell-derived exosomes as a therapeutic tool for cadiovascular disease". World J Stem Cells , 2016; 8(9):1297-395.
International Search Report and the Written Opinion of the International Searching Authority re PCT/US2017/051425.
Wang J. et al. "The novel methods for analysis of exosomes released from endothelial cells and endothelial progenitor cells." Stem Cells Int. Vol 16, 12 pages.
Osada-Oka M. et al. "Macrophage-derived exosomes induce inflammatory factors in endothelial cells under hypertensive conditions." Hypertension Research. (2017) 40, 353-360.

* cited by examiner

*Primary Examiner* — Vanessa L. Ford
*Assistant Examiner* — Sandra E Dillahunt
(74) *Attorney, Agent, or Firm* — Law Office of Christopher Jacob, P.C.

(57) ABSTRACT

The present invention relates to endothelial cell biomarkers and diagnostic and prognostic methods for vascular diseases, including cardiovascular and cerebrovascular diseases. The invention also provides compositions for detecting endothelial cell biomarkers (e.g., endothelial cell-derived exosome biomarkers) as well as compositions and methods useful for treating vascular diseases (e.g., atherosclerotic cerebrovascular disease).

5 Claims, 13 Drawing Sheets

ENDOTHELIAL CELL DERIVED EXOSOMES AND USES THEREOF

RELATED APPLICATIONS

This application claims priority to the U.S. Provisional Patent Application Ser. No. 62/455,582, filed on Feb. 6, 2017, which is hereby incorporated by reference herein in its entirety.

FIELD OF THE INVENTION

The present invention relates to endothelial cell biomarkers and diagnostic and prognostic methods for vascular diseases, including cardiovascular and cerebrovascular diseases. The invention also provides compositions for detecting endothelial cell biomarkers (e.g., endothelial cell-derived exosome biomarkers) as well as compositions and methods useful for treating vascular diseases (e.g., atherosclerotic cerebrovascular disease).

BACKGROUND OF THE INVENTION

Endothelial cells in the monolayer lining all blood vessels have diverse physiological functions, including establishment of a selective barrier between blood and perivascular tissues, provision of an endovascular surface that is non-thrombogenic and minimally adhesive to blood cells, regulation of vascular tone, and regional organization of the proliferation and migration of newly-generated endothelial cells during angiogenesis (Tabas et al. J Cell Biol. 2015; 209:13-22; Boulanger C M. Arterioscler Thromb Vasc Biol. 2016; 36:e26-31; Gimbrone et al. Circ Res. 2016; 118:620-636). A broad range of abnormalities of endothelial cell functions, collectively termed endothelial dysfunction, are fundamental contributors to the pathogenesis of atherosclerosis. The major endothelial abnormalities observed at different stages of atherosclerosis include reduced production of vasoprotective factors such as nitric oxide (NO), generation of inflammatory mediators, altered adherence of platelets and leukocytes, diverse metabolic perturbations, and decreased viability leading to apoptosis (Tabas et al. J Cell Biol. 2015; 209:13-22; Gimbrone et al. Circ Res. 2016; 118:620-636; Pircher et al. Atherosclerosis. 2016; 253:247-257).

Results of analyses of exosomes and ectosomes released by activated and dysfunctional endothelial cells suggest that the contents and functions of exosomes reflect the proteins, RNAs and vascular activities of their cellular source (Rautou et al. Circ Res. 2011; 109:593-606; Dignat-George et al. Arterioscler Thromb Vasc Biol. 2011; 31:27-33; Wang et al. Stem Cells Int. 2016; 2016:2639728). Isolated endothelial exosomes contain functionally relevant levels of cell-surface proteins and other proteins involved in endothelial cell activities, including angiopoietin-2 and the collagen cross-linker lysyl oxidase-2 (Haqqani et al. Fluids Barriers CNS. 2013; 10:4; Ju et al. J Biol Chem. 2014; 289:510-519; de Jong et al. J Cell Mol Med. 2016; 20:342-350). Several protein biomarkers, including GLUT-1, LAT1 and P-glycoprotein, that are localized selectively in the cerebrovascular subset of endothelial cells have recently been identified by the applicant in the total population of plasma endothelial-derived exosomes (Kalaria et al. *Ann Neurol.* 1988; 24:757-764; Pardridge et al. *J Biol Chem.* 1990; 265:18035-18040; Boado et al. *Proc Natl Acad Sci USA.* 1999; 96:12079-12084; Schinkel A H. *Adv Drug Deliv Rev.* 1999; 36:179-194). Such endothelial exosomes also retain the capacities of their endothelial cells of origin to promote monocyte adherence and transendothelial migration, as well as angiogenesis (Boulanger C M. Arterioscler Thromb Vasc Biol. 2016; 36:e26-31; Rautou et al. Circ Res. 2011; 108:335-343). The roles of endothelial-derived exosomes (EDEs) in pathogenesis of atherosclerosis and other vascular diseases should be elucidated further, especially in view of the finding of elevated plasma levels of EDEs in patients with vascular diseases (Chironi et al. Cell Tissue Res. 2009; 335:143-151).

There is a need in the art for biomarkers and methods for detecting endothelial cell abnormalities associated with pathogenesis of vascular diseases. Additionally, there is a need in the art for compositions for detecting biomarkers as well as compositions and methods useful for treating atherosclerosis and other vascular diseases. The present invention meets this need by providing accurate, noninvasive methods for detecting biomarkers that are diagnostic for endothelial cell abnormalities. The present invention further provides novel methods, assays, kits, and compositions for diagnosing, prognosing, predicting, and treating atherosclerosis and other vascular diseases.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention is based on the discovery of biomarkers from endothelial cell-derived exosomes that can be used to detect endothelial cell abnormalities associated with pathogenesis of vascular diseases, including cardiovascular and cerebrovascular diseases. These biomarkers can be used alone or in combination with one or more additional biomarkers or relevant clinical parameters in prognosis, diagnosis, or monitoring treatment of endothelial cell abnormalities associated with vascular diseases.

Biomarkers that can be used in the practice of the invention include, but are not limited to, Tetraspanin-28 (CD81), Vascular Cell Adhesion Molecule 1 (VCAM-1), endothelial Nitric Oxide Synthase (eNOS), Von Willebrand Factor (vWF), Platelet Derived Growth Factor (PDGF), glycoprotein VI (GPVI), Yes Associated Protein (YAP), Tafazzin (TAZ), p-selectin, e-selectin, Angiotensin Converting Enzyme (ACE/CD143), C1qR1/CD93, VE-Cadherin, CC Chemokine Receptor D6, Angiopoietin-2 (Tie-2), Tumor necrosis factor receptor 1 (TNF RI/TNFRSF1A), Tumor necrosis factor receptor 2 (TNF RII/TNFRSF1B), basigin (TRA-1-85/CD147), TRAIL receptor 1 (TRAIL R1/TNFRSF10A), TRAIL receptor 2 (TRAIL R2/TNFRSF10B), Vascular cell adhesion protein 1 (VCAM-1/CD106), VE-Statin, Vascular endothelial growth factor receptor 1 (VEGF R1/Flt-1), Vascular endothelial growth factor receptor 2 (VEGF R2/KDR/Flk-1), Vascular endothelial growth factor receptor 3 (VEGF R3/Flt-4), Signaling lymphocytic activation molecule (SLAM/CD150), Stabilin-1, Stabilin-2, Tumor endothelial marker 7 (TEM7/PLXDC1), Tumor endothelial marker 8 (TEM8/ANTXR1), Thrombomodulin/BDCA-3, Thrombospondin Type 1 Domain Containing 1 (THSD1), Thrombospondin Type 1 Domain Containing 7A (THSD7A), Glucose transporter 1 (GLUT-1), large neutral amino acid transporter (CD98/LAT1), Nitric Oxide Synthase Trafficking Inducer (NOSTRIN), lysyl-oxidase homolog-2 (LOXL2), Large neutral amino acid transporter 1 (LAT-1), and p-glycoprotein. In one embodiment, the invention includes a biomarker panel comprising one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and Permeability-glycoprotein (p-glycoprotein).

In some embodiments, the present invention provides a method of detecting markers in a biological sample, the method comprising: a) providing a biological sample comprising endothelial-derived exosomes from a subject having a cardiovascular or cerebrovascular disease; and b) detecting the presence of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein in the sample. A method comprising: a) providing a biological sample comprising endothelial-derived exosomes from a subject having a cardiovascular or cerebrovascular disease; b) enriching the sample for endothelial-derived exosomes; and c) detecting the presence of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Angiopoietin-2 (Tie-2), TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, and p-glycoprotein in the sample. In some embodiments, the methods of the present invention further comprise determining the level or concentration of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein in the sample.

In some embodiments, the present invention provides a method of detecting markers in a biological sample, the method comprising: a) providing a biological sample comprising endothelial-derived exosomes from a subject having a cardiovascular or cerebrovascular disease; b) isolating endothelial cell-derived exosomes from the biological sample; and c) detecting the presence of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein in the exosomes. In some embodiments, the one or more biomarkers comprises VCAM-1, vWF, PDGF, Tie-2, GLUT-1, and LOXL-2. In some embodiments, the one or more biomarkers comprises GLUT-1, LAT-1, P-gp, VCAM-1, and NOSTRIN. In some embodiments, the one or more biomarkers comprises VCAM-1, Tie-2, and LOXL-2. In some embodiments, the one or more biomarkers comprises GLUT-1, LAT-1, and P-gp.

In other embodiments, the present invention provides a method of detecting markers in a biological sample, the method comprising: a) providing; i) a biological sample comprising endothelial-derived exosomes from a subject having a cardiovascular or cerebrovascular disease and ii) immunoassay reagents for the detection of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein; and b) detecting the presence of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein in the sample using said reagents. In some embodiments, the one or more biomarkers comprises VCAM-1, vWF, PDGF, Tie-2, GLUT-1, and LOXL-2. In some embodiments, the one or more biomarkers comprises GLUT-1, LAT-1, P-gp, VCAM-1, and NOSTRIN. In some embodiments, the one or more biomarkers comprises VCAM-1, Tie-2, and LOXL-2. In some embodiments, the one or more biomarkers comprises GLUT-1, LAT-1, and P-gp.

In other embodiments, the present invention provides a method of detecting markers in a biological sample, the method comprising: a) providing; i) a biological sample comprising endothelial-derived exosomes from a subject having a cardiovascular or cerebrovascular disease and ii) immunoassay reagents for detection of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/

CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOS-TRIN, LOXL2, LAT-1, and p-glycoprotein; b) isolating endothelial cell-derived exosomes from the biological sample and c) detecting the presence of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOS-TRIN, LOXL2, LAT-1, and p-glycoprotein in the exosomes using said reagents. In some embodiments, the one or more biomarkers comprises VCAM-1, vWF, PDGF, Tie-2, GLUT-1, and LOXL-2. In some embodiments, the one or more biomarkers comprises GLUT-1, LAT-1, P-gp, VCAM-1, and NOSTRIN. In some embodiments, the one or more biomarkers comprises VCAM-1, Tie-2, and LOXL-2. In some embodiments, the one or more biomarkers comprises GLUT-1, LAT-1, and P-gp.

In some embodiments, the reagents comprise antibodies for performing an immunoassay. In some embodiments, the immunoassay is selected from the group consisting of an ELISA, radio-immunoassay, automated immunoassay, cytometric bead assay, and immunoprecipitation assay. In other embodiments, the biological sample can be any bodily fluid comprising endothelial cell-derived exosomes, including, but not limited to, whole blood, plasma, serum, lymph, amniotic fluid, urine, saliva, and umbilical cord blood. In some embodiments, the marker is a full size marker. In other embodiments said marker is a fragment of the full size marker. In other embodiments, the detecting the presence of the marker in the biological sample comprises detecting the amount of the marker in the biological sample. In some embodiments, the method further comprises the step of determining a treatment course of action based on the diagnosis of a cardiovascular or cerebrovascular disease.

In some embodiments, the subject has been diagnosed with a cardiovascular or cerebrovascular disease or suspected of having a cardiovascular and cerebrovascular disease, which may include, but not limited to, atherosclerosis, coronary artery disease, thrombosis, thrombophlebitis, embolism, infarction, stroke, transient ischemic attack (TIA), vascular dementia, senile dementia, and Alzheimer's disease. In other embodiments, the subject has an infection (e.g., severe, chronic or systemic infection), inflammation, other severe disease, or other condition putting the subject at risk of developing a cardiovascular and cerebrovascular disease. In other embodiments, the subject is at-risk of developing a cardiovascular or cerebrovascular disease, which may include, but not limited to, atherosclerosis, coronary artery disease, thrombosis, thrombophlebitis, embolism, infarction, stroke, transient ischemic attack, vascular dementia, senile dementia, and Alzheimer's disease.

In some embodiments, isolating endothelial cell-derived exosomes from the biological sample comprises: contacting the biological sample with an agent under conditions wherein an endothelial cell-derived exosome present in the biological sample binds to the agent to form an endothelial cell-derived exosome-agent complex; and isolating the endothelial cell-derived exosome from the endothelial cell-derived exosome-agent complex to obtain a sample containing the endothelial cell-derived exosome, wherein the purity of the endothelial cell-derived exosomes present in said sample is greater than the purity of the endothelial cell-derived exosomes present in said biological sample. The agent may be an antibody that specifically binds to an endothelial cell-derived exosome surface marker (e.g., CD105, CD31, or CD146). Example 1 describes isolation of endothelial cell-derived exosomes from a biological sample, for example, by immunoabsorption using an anti-human CD31 antibody and an anti-human CD146 antibody specific for these constitutively expressed surface protein. In other embodiments, endothelial cell-derived exosomes are isolated by immunoabsorption using an anti-human CD105 antibody specific for this constitutively expressed surface protein.

Biomarker proteins can be measured, for example, by performing immunohistochemistry, immunocytochemistry, immunofluorescence, immunoprecipitation, Western blotting, or an enzyme-linked immunosorbent assay (ELISA). In certain embodiments, the level of a biomarker is measured with an immunoassay. For example, the level of the biomarker can be measured by contacting an antibody with the biomarker, wherein the antibody specifically binds to the biomarker, or a fragment thereof containing an antigenic determinant of the biomarker. Antibodies that can be used in the practice of the invention include, but are not limited to, monoclonal antibodies, polyclonal antibodies, chimeric antibodies, recombinant fragments of antibodies, Fab fragments, Fab' fragments, F(ab')2 fragments, $F_v$ fragments, or $scF_v$ fragments. In one embodiment, the method comprises measuring amounts of an in vitro complex comprising a labeled antibody bound to an endothelial cell-derived exosome biomarker. In one aspect, the endothelial cell-derived exosome biomarker is selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein. In some embodiments, increased levels of the biomarker CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein compared to reference value ranges of the biomarkers for a control subject indicate that the patient has a cardiovascular or cerebrovascular disease. In some aspects, the control subject is a subject without a cardiovascular or cerebrovascular disease. In some embodiments, the endothelial cell-derived exosome biomarker comprises VCAM-1, vWF, PDGF, Tie-2, GLUT-1, and LOXL-2. In some embodiments, the endothelial cell-derived exosome biomarker comprises GLUT-1, LAT-1, P-gp, VCAM-1, and NOSTRIN. In some embodiments, the one or more biomarkers comprises VCAM-1, Tie-2, and LOXL-2. In some embodiments, the one or more biomarkers comprises GLUT-1, LAT-1, and P-gp.

The levels of the biomarkers from endothelial cell-derived exosomes from a subject can be compared to reference value ranges for the biomarkers found in one or more samples of endothelial cell-derived exosomes from one or more subjects without a cardiovascular or cerebrovascular disease (e.g., control sample, healthy subject without vascular disease). Alternatively, the levels of the biomarkers from endothelial cell-derived exosomes from a subject can be compared to reference values ranges for the biomarkers found in one or more samples of endothelial cell-derived exosomes from one or more subjects with a cardiovascular or cerebrovascular disease.

In some embodiments, the invention provides a method for monitoring the efficacy of a therapy for treating a cardiovascular or cerebrovascular disease in a patient, the method comprising: a) providing a first biological sample comprising endothelial cell-derived exosomes from the patient before the patient undergoes the therapy and a second biological sample comprising endothelial cell-derived exosomes after the patient undergoes the therapy; b) isolating endothelial cell-derived exosomes from the first biological sample and the second biological sample; and c) detecting one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein for the endothelial cell-derived exosomes from the first biological sample and the second biological sample; and d) comparing the levels of the one or more biomarkers for the endothelial cell-derived exosomes from the first biological sample to the levels of the one or more biomarkers for the endothelial cell-derived exosomes from the second biological sample, wherein decreased levels of the one or more biomarkers for the endothelial cell-derived exosomes from the second biological sample compared to the levels of the one or more biomarkers for the endothelial cell-derived exosomes from the first biological sample indicate that the patient is improving, and increased levels of the one or more biomarkers for the endothelial cell-derived exosomes from the second biological sample compared to the levels of the one or more biomarkers for the endothelial cell-derived exosomes from the first biological sample indicate that the patient is worsening or not responding to the therapy. In some embodiments, the one or more biomarkers comprises VCAM-1, vWF, PDGF, Tie-2, GLUT-1, and LOXL-2. In some embodiments, the one or more biomarkers comprises GLUT-1, LAT-1, P-gp, VCAM-1, and NOSTRIN. In some embodiments, the one or more biomarkers comprises VCAM-1, Tie-2, and LOXL-2. In some embodiments, the one or more biomarkers comprises GLUT-1, LAT-1, and P-gp.

In other embodiments, the invention provides a method for monitoring a cardiovascular or cerebrovascular disease in a subject, the method comprising: a) measuring levels of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein from endothelial cell-derived exosomes from a first biological sample from the subject, wherein the first biological sample is obtained from the subject at a first time point; b) measuring levels of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein from endothelial cell-derived exosomes from a second biological sample from the subject, wherein the second biological sample is obtained from the subject at a second (i.e., later) time point; and c) comparing the levels of the biomarkers for endothelial cell-derived exosomes from the first biological sample to the levels of the biomarkers for endothelial cell-derived exosomes from the second biological sample, wherein decreased levels of the one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein from the endothelial cell-derived exosomes from the second biological sample compared to the levels of the biomarkers in the first biological sample indicate that the patient is improving, and increased levels of the one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein from the endothelial cell-derived exosomes from the second biological sample compared to the levels of the biomarkers for the endothelial cell-derived exosomes from the first biological sample indicate that the patient is worsening. In some embodiments, the one or more biomarkers comprises VCAM-1, vWF, PDGF, Tie-2, GLUT-1, and LOXL-2. In some embodiments, the one or more biomarkers comprises GLUT-1, LAT-1, P-gp, VCAM-1, and NOSTRIN. In some embodiments, the one or more biomarkers comprises VCAM-1, Tie-2, and LOXL-2. In some embodiments, the one or more biomarkers comprises GLUT-1, LAT-1, and P-gp.

In yet other embodiments, the invention provides a method of treating a patient suspected of having a cardiovascular or cerebrovascular disease, the method comprising: a) detecting endothelial cell abnormalities in the patient or receiving information regarding the endothelial cell abnormalities status of the patient, as determined according to a method described herein; and b) administering a therapeutically effective amount of at least one drug that inhibits endothelial cell abnormalities to the subject if endothelial cell abnormalities are detected in the subject. After treatment, the method may further comprise monitoring the response of the patient to treatment.

In other embodiments, the invention provides a method comprising: providing a biological sample from a subject suspected of having a cardiovascular or cerebrovascular disease; detecting the presence or level of at least one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein; and administering a treatment to the subject. In one embodiment, the method further comprises administering a therapeutically effective amount of at least one drug that treats a cardiovascular or cerebrovascular disease to the subject if increased levels of the one or more biomarkers are detected in the subject. After treatment, the method may further comprise monitoring the response of the subject to treatment. In some embodiments, the one or more biomarkers comprises VCAM-1, vWF, PDGF, Tie-2, GLUT-1, and LOXL-2. In some embodiments, the one or more biomarkers comprises GLUT-1, LAT-1, P-gp, VCAM-1, and NOSTRIN. In some embodiments, the one or more biomarkers comprises VCAM-1, Tie-2, and LOXL-2. In some embodiments, the one or more biomarkers comprises GLUT-1, LAT-1, and P-gp.

In other embodiments, the present invention provides a method of treating a subject with a cardiovascular or cerebrovascular disease, comprising: providing a biological sample from the subject; determining the level of at least one or more biomarkers selected from the list consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein using at least one reagent that specifically binds to said biomarkers; and prescribing a treatment regimen based on the level of the one or more biomarkers. In some embodiments, the method further comprises isolating endothelial cell-derived exosomes from the biological sample. In some embodiments, the vascular disease is selected from the group consisting of atherosclerosis, coronary artery disease, thrombosis, thrombophlebitis, embolism, infarction, stroke, transient ischemic attack (TIA), vascular dementia, senile dementia, and Alzheimer's disease. In some embodiments, the one or more biomarkers comprises VCAM-1, vWF, PDGF, Tie-2, GLUT-1, and LOXL-2. In some embodiments, the one or more biomarkers comprises GLUT-1, LAT-1, P-gp, VCAM-1, and NOSTRIN. In some embodiments, the one or more biomarkers comprises VCAM-1, Tie-2, and LOXL-2. In some embodiments, the one or more biomarkers comprises GLUT-1, LAT-1, and P-gp.

In some embodiments, the invention provides a set of biomarkers for assessing cardiovascular or cerebrovascular disease status of a subject, the set comprising one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein, wherein endothelial cell-derived exosome levels of the biomarkers in the set are assayed; and wherein the biomarker levels of the set of biomarkers determine the cardiovascular or cerebrovascular disease status of the subject with at least 40%, 50%, 60%, 70%, 75%, 80%, 85%, 90%, 95%, 99%, or 100% specificity. In some aspects, the set of biomarkers determine the cardiovascular or cerebrovascular disease status of the subject with at least 40%, 50%, 60%, 70%, 75%, 80%, 85%, 90%, 95%, 99%, or 100% sensitivity. In yet other aspects, the set of biomarkers determine the cardiovascular or cerebrovascular disease status of the subject with at least 40%, 50%, 60%, 70%, 75%, 80%, 85%, 90%, 95%, 99%, or 100% accuracy. In some embodiments, the one or more biomarkers comprises VCAM-1, vWF, PDGF, Tie-2, GLUT-1, and LOXL-2. In some embodiments, the one or more biomarkers comprises GLUT-1, LAT-1, P-gp, VCAM-1, and NOSTRIN. In some embodiments, the one or more biomarkers comprises VCAM-1, Tie-2, and LOXL-2. In some embodiments, the one or more biomarkers comprises GLUT-1, LAT-1, and P-gp.

In other embodiments, the invention provides a composition comprising at least one in vitro complex comprising a labeled antibody bound to a biomarker protein selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein, wherein said biomarker protein is extracted from endothelial cell-derived exosomes of a subject who has been diagnosed with a cardiovascular or cerebrovascular disease, suspected of having a cardiovascular or cerebrovascular disease, or at risk of developing a cardiovascular or cerebrovascular disease. The antibody may be detectably labeled with any type of label, including, but not limited to, a fluorescent label, an enzyme label, a chemiluminescent label, or an isotopic label. In some embodiments, the composition is in a detection device (i.e., device capable of detecting labeled antibody). In another embodiment, the subject has endothelial cell abnormalities. In some embodiments, the biomarker protein comprises VCAM-1, vWF, PDGF, Tie-2, GLUT-1, and LOXL-2. In some embodiments, the biomarker protein comprises GLUT-1, LAT-1, P-gp, VCAM-1, and NOSTRIN. In some embodiments, the one or more biomarkers comprises VCAM-1, Tie-2, and LOXL-2. In some embodiments, the one or more biomarkers comprises GLUT-1, LAT-1, and P-gp.

In other embodiments, the invention provides a kit for detecting or monitoring a cardiovascular or cerebrovascular disease in a subject. In some embodiments, the kit may include a container for holding a biological sample isolated from a subject who has been diagnosed or suspected of having a cardiovascular or cerebrovascular disease or at risk of developing a cardiovascular or cerebrovascular disease, at least one agent that specifically detects a biomarker of the present invention; and printed instructions for reacting the agent with endothelial cell-derived exosomes from the biological sample or a portion of the biological sample to detect the presence or amount of at least one biomarker. In other embodiments, the kit may also comprise one or more agents that specifically bind endothelial cell-derived exosomes for use in isolating endothelial cell-derived exosomes from a biological sample. In yet other embodiments, the kit may further comprise one or more control reference samples and reagents for performing an immunoassay. In certain embodiments, the agents may be packaged in separate containers. In some embodiments, the kit comprises agents for measuring the levels of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein. In yet other embodiments, the kit further comprises an antibody that binds to an endothelial cell-derived exosome surface marker (e.g., CD105, CD31, or CD146).

In other embodiments, the invention provides a method for treating a cardiovascular or cerebrovascular disease, the method comprising the steps of: providing a biological sample from a subject suspected of having a cardiovascular or cerebrovascular disease, wherein the sample comprises endothelial cell-derived exosomes; measuring the level of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein from the biological sample, wherein an altered level of the one or more biomarkers in the sample relative to the level in a control sample is indicative of a need for treatment; and administering an effective amount of an agent to the subject thereby treating the cardiovascular or cerebrovascular disease in the subject.

These and other embodiments of the present invention will readily occur to those of skill in the art in light of the disclosure herein, and all such embodiments are specifically contemplated.

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

Figure 1A:
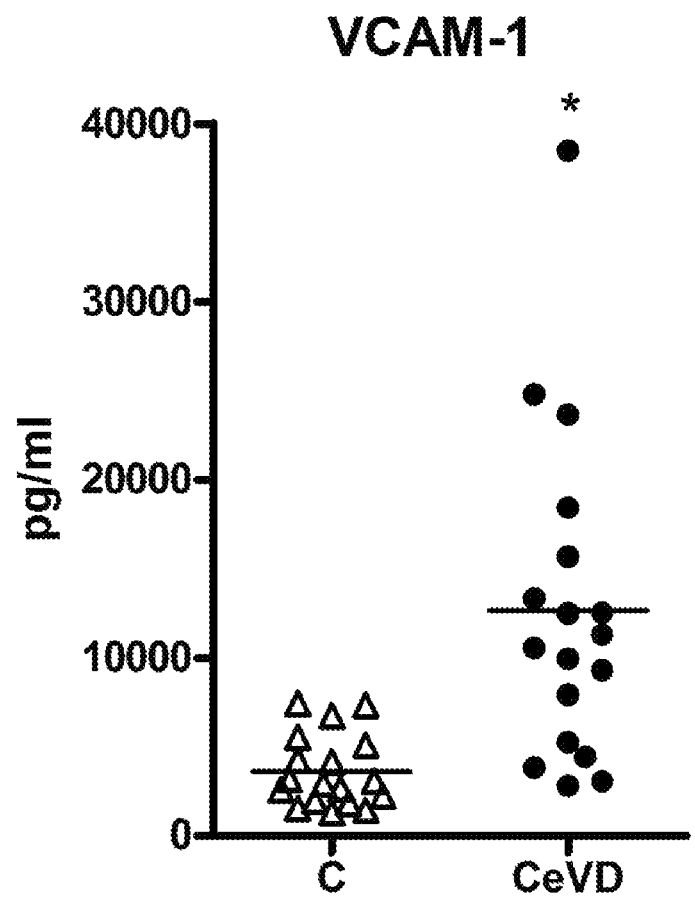
FIGS. 1A-1F set forth data showing levels of endothelial cell biomarkers and proteins implicated in atherosclerosis in plasma EDEs of patients with cerebrovascular disease (CeVD) relative to those of matched controls without cerebrovascular disease (C). Each point represents the value for one of the patients or controls and horizontal lines depict the respective mean levels. The significance of differences between levels for CeVD patients and controls was calculated by an unpaired t test; *, p<0.001 and **, p<0.0001.
Figure 1B:
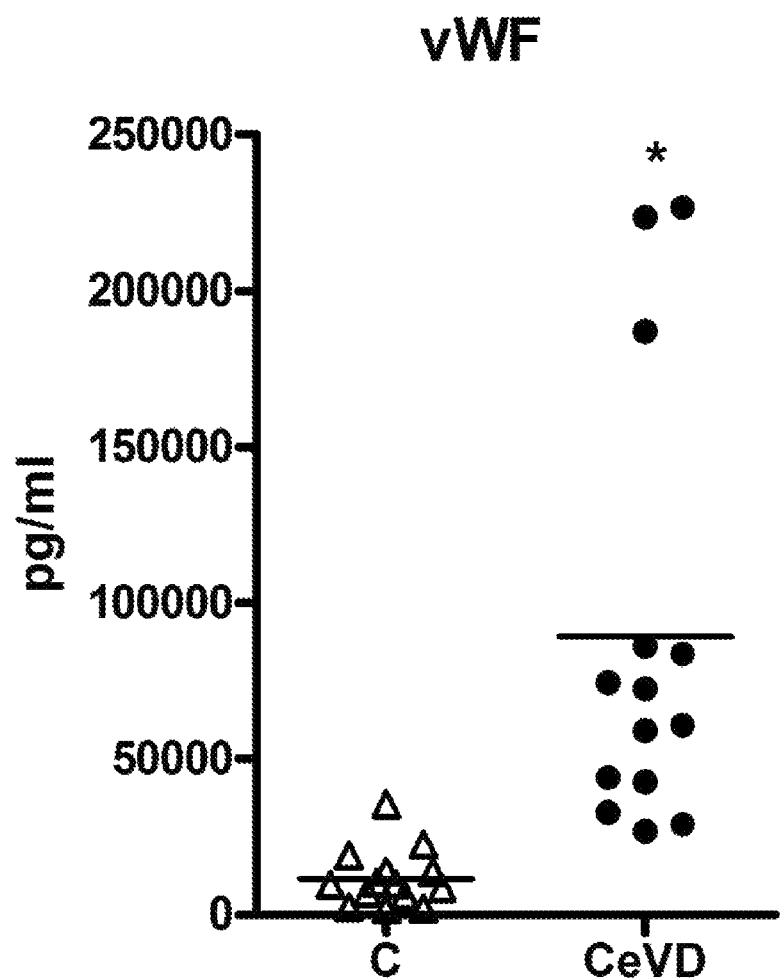
Figure 1C:
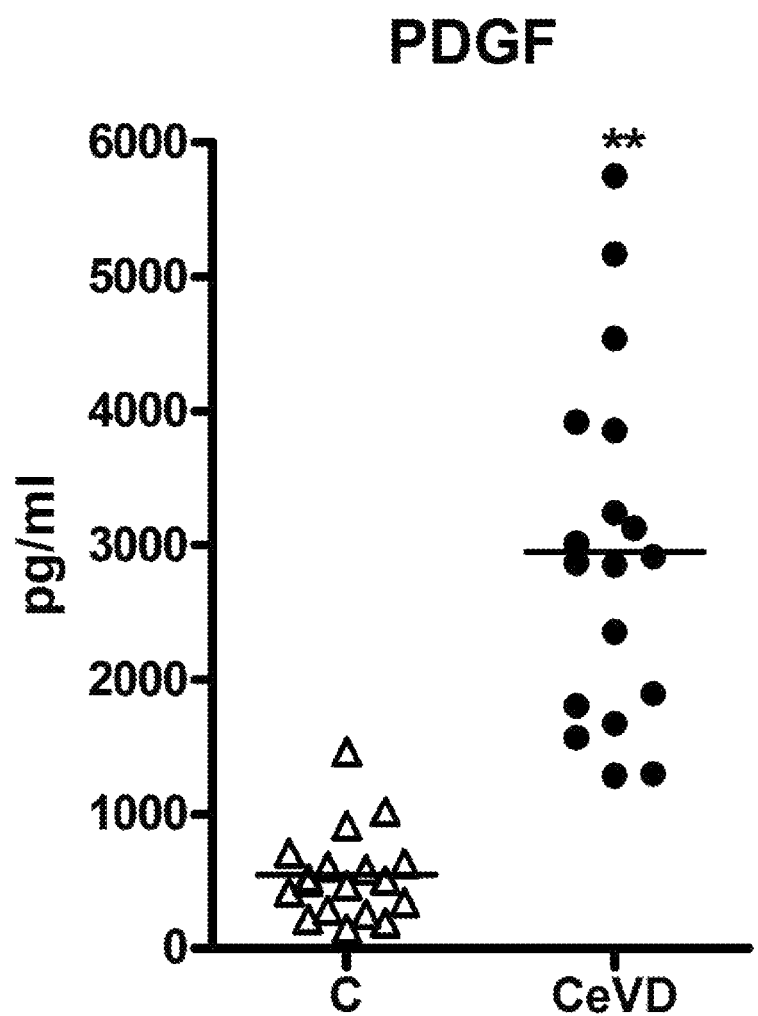
Figure 1D:
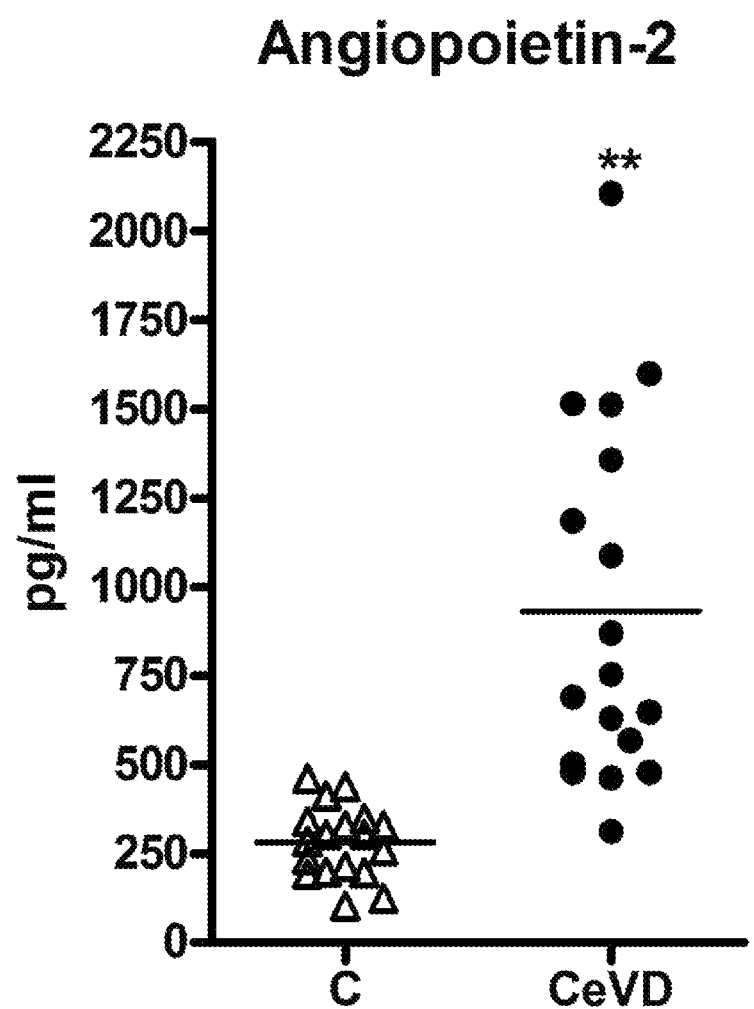
Figure 1E:
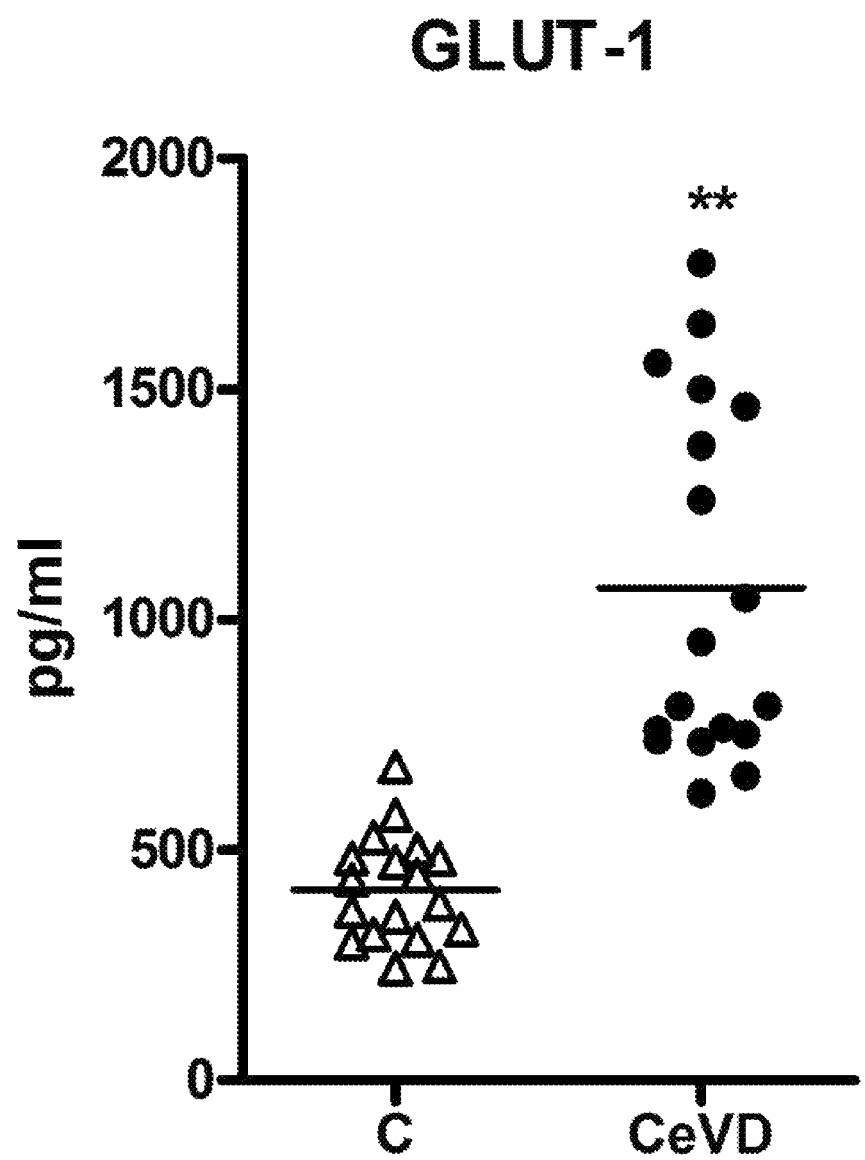
Figure 1F:
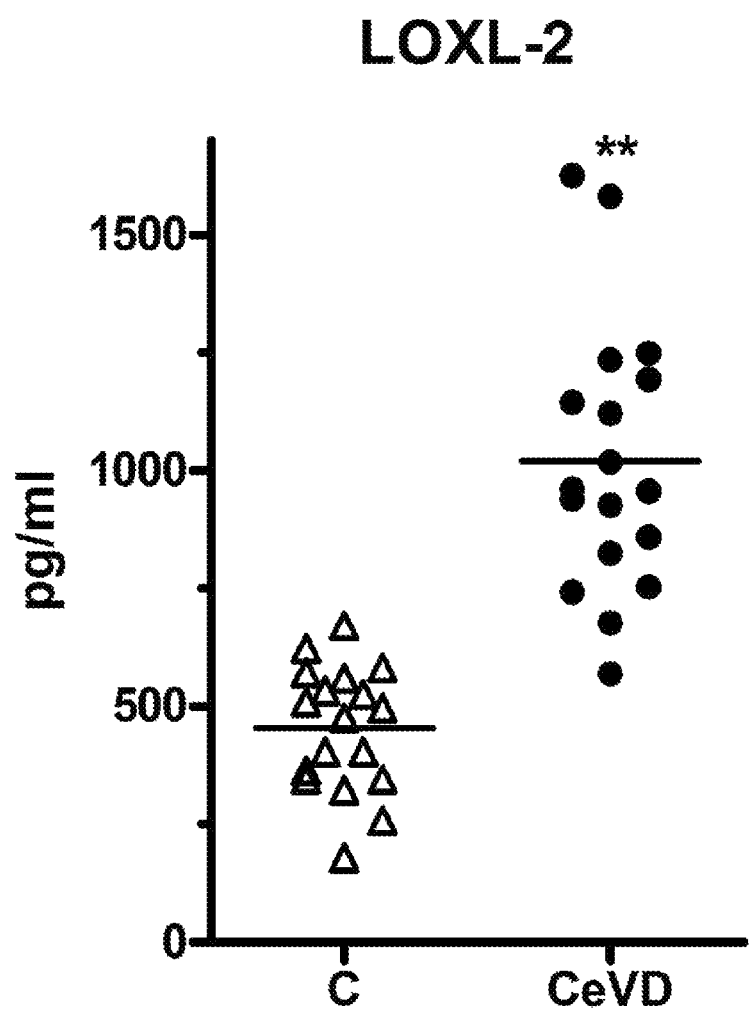
Figure 2A:
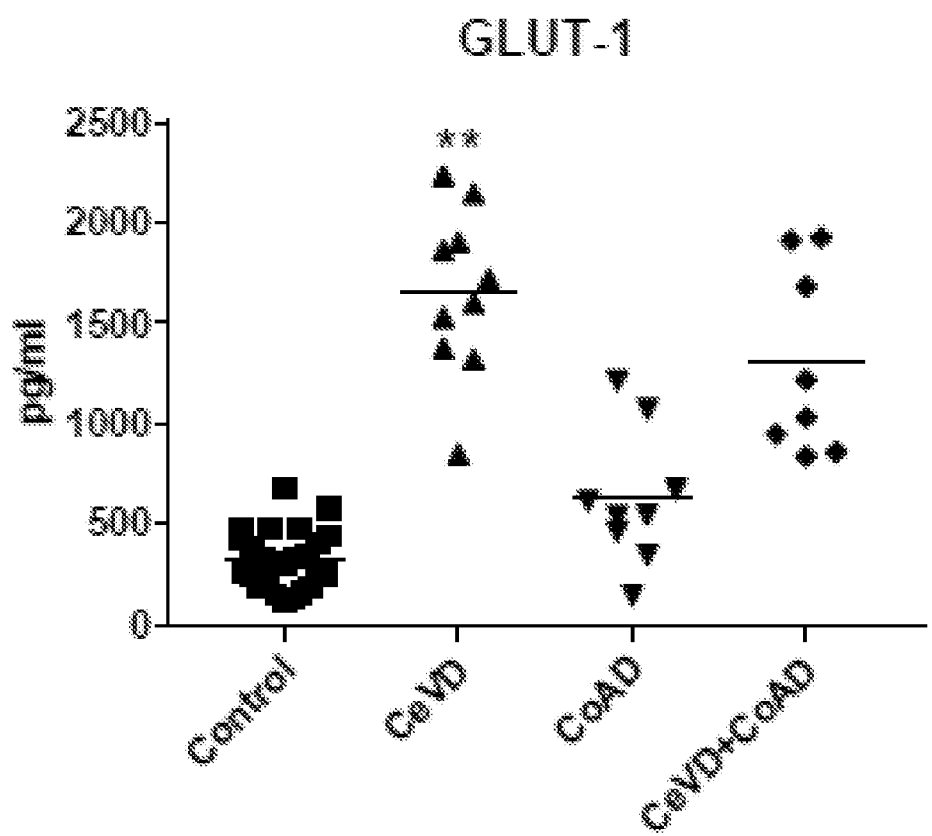
FIGS. 2A-2E set forth data showing higher levels of cerebrovascular (CV)-selective endothelial cell biomarkers (GLUT-1, LAT-1, P-gp) in plasma endothelial-derived exosomes (EDEs) of patients with cerebrovascular disease (CeVD) than patients with coronary artery disease (CoAD). Each point depicts the plasma EDE level of a protein biomarker for control subjects (C, n=25) without detectable vascular disease and of the same age and gender range as patients, and patients with CeVD (n=10), CoAD (n=10) or both conditions (n=8). The horizontal line in each point cluster represents the mean for the group. The significant differences between CV-selective EDE biomarker levels of patients with CeVD and those with CoAD alone were calculated with a two-sample t test; *, p<0.01 and **, p<0.0001. The mean of every set of biomarker levels for patients was significantly higher than the respective mean for Cs with a p value<0.0001, except for the set of GLUT-1 levels of CoAD patients compared to those of Cs where the p value was only <0.01.
Figure 2B:
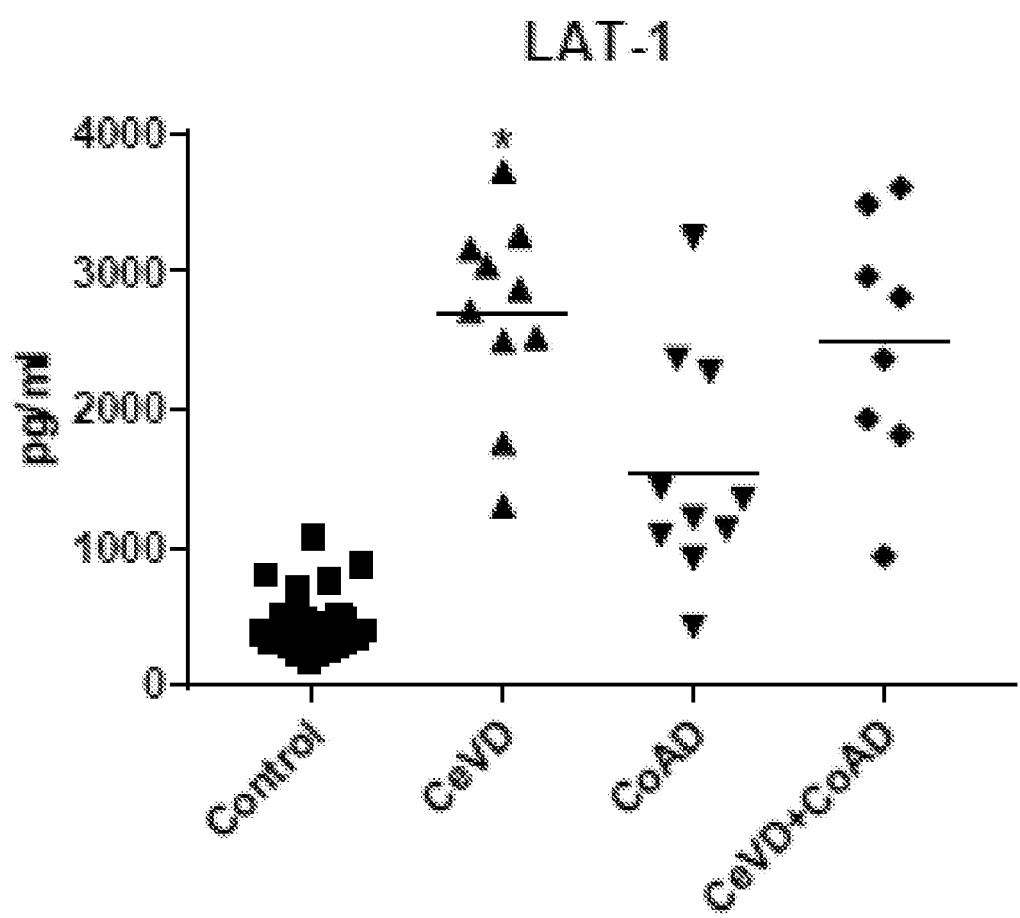
Figure 2C:
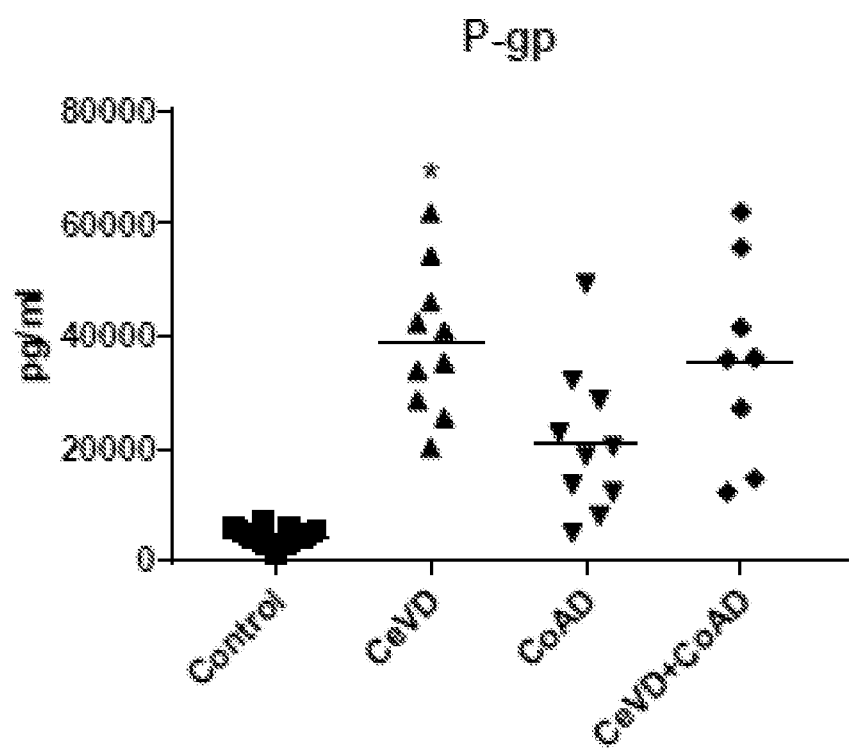
Figure 2D:
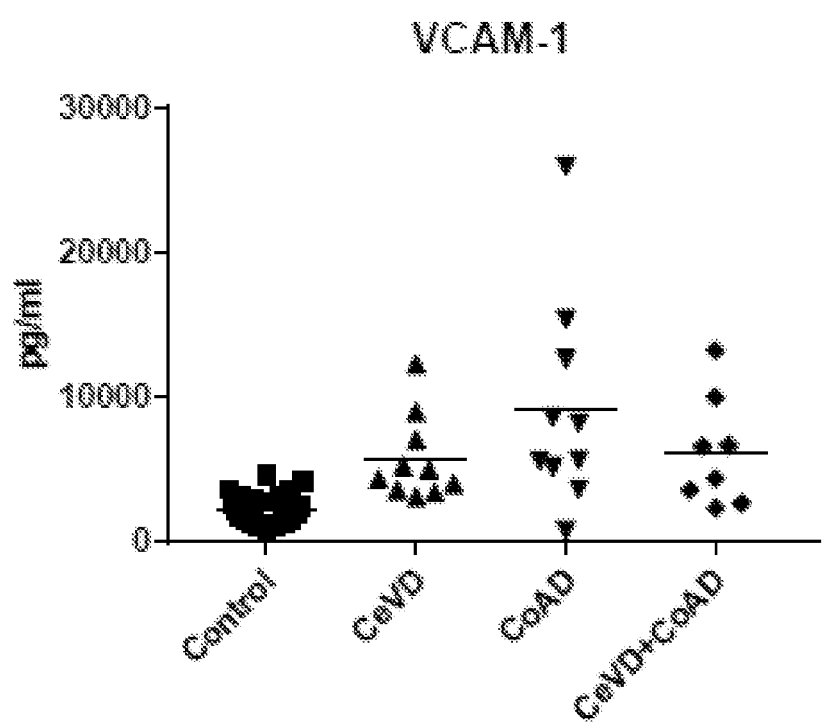
Figure 2E:
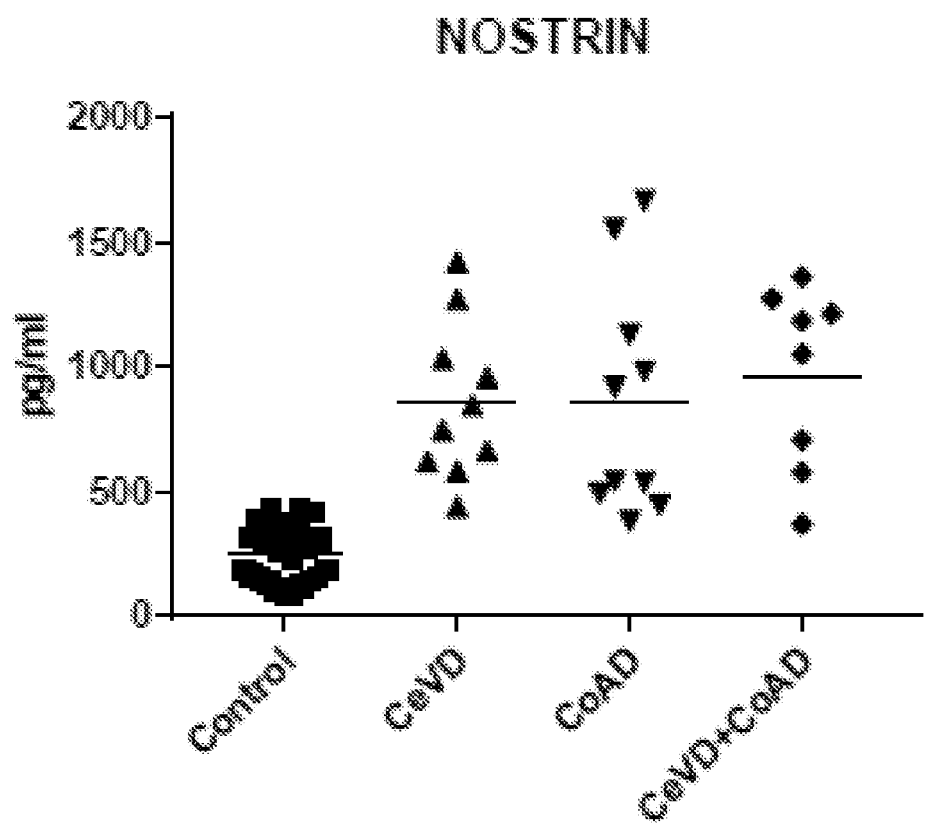

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items. It must be noted that as used herein and in the appended claims, the singular forms "a," "an," and "the" include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

DESCRIPTION OF THE INVENTION

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The present invention relates, in part, to the discovery that endothelial cell-derived exosomal biomarkers can be used to detect endothelial cell abnormalities associated with pathogenesis of vascular diseases, including cardiovascular and cerebrovascular diseases. The inventor has demonstrated that endothelial cell-derived exosome (EDE) levels of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein are altered in subjects with cerebrovascular disease (see Example 1).

The present invention also provides compositions for use in the methods described herein. Such compositions may include small molecule compounds; peptides and proteins including antibodies or functionally active fragments thereof.

The present invention further provides kits for detecting endothelial cell abnormalities in a subject, identifying a subject at risk of a vascular disorder associated with endothelial cell abnormalities, or prescribing a therapeutic regimen or predicting benefit from therapy in a subject having a vascular disorder or at risk of developing a vascular disorder. In these embodiments, the kits comprise one or more antibodies which specifically bind endothelial cell-derived exosomes, one or more antibodies which specifically bind an endothelial cell-derived exosomal biomarker of the present invention, one or more containers for collecting and or holding the biological sample, and instructions for the kits use.

The section headings are used herein for organizational purposes only, and are not to be construed as in any way limiting the subject matter described herein.

Biological Sample

The present invention provides biomarkers and diagnostic and prognostic methods for vascular diseases. Biomarker are detected from endothelial cell-derived exosomes from a biological sample obtained from a subject. Biological samples can include any bodily fluid comprising exosomes, including, but not limited to, whole blood, plasma, serum, lymph, amniotic fluid, and umbilical cord blood.

In some embodiments, the biological sample of the invention can be obtained from blood. In some embodiments, about 1-10 mL of blood is drawn from a subject. In other embodiments, about 10-50 mL of blood is drawn from a subject. Blood can be drawn from any suitable area of the body, including an arm, a leg, or blood accessible through a central venous catheter. In some embodiments, blood is collected following a treatment or activity. For example, blood can be collected following a medical exam. The timing of collection can also be coordinated to increase the number and/or composition of endothelial cell-derived exosomes present in the sample. For example, blood can be collected following exercise or a treatment that induces vascular dilation.

Blood may be combined with various components following collection to preserve or prepare samples for subsequent techniques. For example, in some embodiments, blood is treated with an anticoagulant, a cell fixative, a protease inhibitor, a phosphatase inhibitor, or preservative(s) for protein or DNA or RNA following collection. In some embodiments, blood is collected via venipuncture using a needle and a syringe that is emptied into collection tubes containing an anticoagulant such as EDTA, heparin, or acid citrate dextrose (ACD). Blood can also be collected using a heparin-coated syringe and hypodermic needle. Blood can also be combined with components that will be useful for cell culture. For example, in some embodiments, blood is combined with cell culture media or supplemented cell culture media (e.g., cytokines). In certain embodiments, platelet-rich plasma (PRP) is mixed with PBS to block ex vivo platelet activation before centrifugation to yield platelet-poor plasma (PPP).

Enrichment or Isolation of Endothelial Cell-Derived Exosomes

Samples can be enriched for endothelial cell-derived exosomes through positive selection, negative selection, or a combination of positive and negative selection. In some embodiments, exosomes are directly captured. In other embodiments, blood cells are captured and exosomes are collected from the remaining biological sample.

Samples can also be enriched for exosomes based on the biochemical properties of exosomes. The first step is physical isolation entailing polymer precipitation with centrifugation in one or two cycles. Then, for example, samples can be enriched for exosomes based on differences in antigens. In some of the embodiments, antibody-conjugated magnetic or paramagnetic beads in magnetic field gradients or fluorescently labeled antibodies with flow cytometry are used. In some of the embodiments based on metabolic differences, dye uptake/exclusion measured by flow cytometry or another sorting technology is used. Samples can also be enriched for exosomes based on other biochemical properties known in the art. For example, samples can be enriched for exosomes using ligands or soluble receptors.

In some embodiments, surface markers are used to positively enrich endothelial cell-derived exosomes in the sample. In other embodiments, cell surface markers that are not found on exosomes are used to negatively enrich exosomes by depleting cell populations. Modified versions of flow cytometry sorting may also be used to further enrich for endothelial cell-derived exosomes using surface markers or intracellular or extracellular markers conjugated to fluorescent labels. Intracellular and extracellular markers may include nuclear stains or antibodies against intracellular or extracellular proteins preferentially expressed in exosomes. Cell surface markers may include cell surface antigens that are preferentially expressed on endothelial cell-derived exosomes. In some embodiments, the cell surface marker is an endothelial cell-derived exosome surface marker, including, for example, CD105, CD31, and CD146. In some embodiments, a monoclonal antibody that specifically binds to CD105, CD31, or CD146 is used to enrich or isolate endothelial cell-derived exosomes from the sample. In certain aspects, the antibody against CD105, CD31, or CD146 is biotinylated. In this embodiment, the biotinylated antibody can form an antibody-exosome complex that can be subsequently isolated using streptavidin-agarose resin or beads. In other embodiments, the antibody is a monoclonal anti-human CD105, CD31, or CD146 antibody.

In other embodiments, endothelial cell-derived exosomes are isolated or enriched from a biological sample comprising: contacting a biological sample with an agent under conditions wherein an endothelial cell-derived exosome present in said biological sample binds to said agent to form an exosome-agent complex; and isolating said exosome from said exosome-agent complex to obtain a sample containing said exosome, wherein the purity of the exosomes present in the sample is greater than the purity of exosomes present in the biological sample. In certain embodiments, the exosomes are endothelial cell-derived exosomes. In certain embodiments, the agent is an antibody or a lectin. Lectins useful for forming an exosome-lectin complex are described in U.S. Patent Application Publication No. 2012/0077263. In some embodiments, multiple isolating or enriching steps are performed. In certain aspects of the present embodiment, a first isolating step is performed to isolate exosomes from a blood sample freed of plasma membrane-derived membrane vesicles and a second isolating step is performed to isolate endothelial cell-derived exosomes from other exosomes. In other embodiments, the exosome portion of the exosome-agent complex is lysed using a lysis reagent and the protein levels of the lysed exosome are assayed. In some embodiments, the antibody-exosome complex is created on a solid phase. In yet other embodiments, the methods further comprise releasing the exosome from the antibody-exosome complex. In certain embodiments, the solid phase is non-magnetic beads, magnetic beads, agarose, or sepharose. In other embodiments, the vesicle is released by exposing the antibody-exosome complex to low pH between 3.5 and 1.5. In yet other embodiments, the released exosome is neutralized by adding a high pH solution. In other embodiments, the released exosomes are lysed by incubating the released exosomes with a lysis solution. In still other embodiments, the lysis solution contains inhibitors for proteases and phosphatases.

Vascular Disorders

The present invention provides methods for detecting endothelial cell abnormalities associated with a vascular disorder in a subject and identifying a subject at risk of developing a vascular disorder due to endothelial cell abnormalities, or prescribing a therapeutic regimen or predicting benefit from therapy. High levels of endothelial cell abnormalities in vivo result in elevated endothelial-derived exosomal cargo levels of cytoadhesive, thrombogenic, and inflammatory factors, which can accelerate formation of vascular plaques, clots, and strictures. Hence, endothelial cell abnormalities are associated with development or worsening of a vascular disorder. Accordingly, detection of endothelial cell abnormalities can be used to identify individuals who will benefit from therapy.

In some embodiments the vascular disorder is a cardiovascular disorder or a cerebrovascular disorder such as, but not limited to, atherosclerosis, coronary artery disease, thrombosis (e.g., venous thrombosis and arterial thrombosis), thrombocytosis, thrombophlebitis, embolism (e.g., pulmonary embolism and venous thromboembolism), infarction (e.g., myocardial infarction and cerebral infarction), stroke, transient ischemic attack, myeloproliferative diseases, vascular dementia, senile dementia, and Alzheimer's disease.

Endothelial cell abnormalities may also be associated with an infection (e.g., severe, chronic or systemic infection), inflammation, or severe disease, which increases the risk of developing a vascular disorder. For example, endothelial cell abnormalities associated with sepsis, acute respiratory distress syndrome, hepatitis B virus (HBV) infection, pneumonia, or an opportunistic infection in an immunocompromised or immunodeficient patient (e.g., infected with human immunodeficiency virus (HIV)) can lead to venous thrombosis and arterial thrombosis as well as organ failure. Additionally, risk factors for developing a vascular disorder include diabetes mellitus, cigarette smoking, high blood pressure, abnormal lipid panel, increased fasting blood glucose, and a family history of premature death due to cardiovascular causes. Patients with such risk factors may benefit from testing for endothelial cell abnormalities by the methods described herein.

In some embodiments, the present invention enables a medical practitioner to diagnose or prognose one or more vascular disorders in a subject. In yet other embodiments, the present invention enables a medical practitioner to identify a subject at risk of developing a vascular disorder associated with endothelial cell abnormalities. In other embodiments, the present invention enables a medical practitioner to predict whether a subject will later develop a vascular disorder. In further embodiments the present invention enables a medical practitioner to prescribe a therapeutic regimen or predict benefit from therapy in a subject having a vascular disorder or at risk of developing a vascular disorder.

In certain embodiments, the subject is a mammalian subject, including, e.g., a cat, a dog, a rodent, etc. In preferred embodiments, the subject is a human subject.

Biomarkers

Endothelial-derived exosomal cargo levels of biomarker proteins are assayed for a subject having or at-risk of having a vascular disorder. In some embodiments, one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein are assayed in order to detect whether or not a subject has a cardiovascular or cerebrovascular disease. In one embodiment, all of the biomarkers, CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein, are assayed in combination to detect a cardiovascular or cerebrovascular disease.

One of ordinary skill in the art has several methods and devices available for the detection and analysis of the biomarkers of the instant invention. With regard to polypeptides or proteins in patient test samples, immunoassay devices and methods are often used. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, planar waveguide technology, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the biomarkers is also contemplated by the present invention. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of biomarkers may be carried out separately or simultaneously with one test sample. Several biomarkers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in biomarker levels, as well as the absence of change in biomarker levels, would provide useful information about disease status that includes, but is not limited to the appropriateness of drug therapies, the effectiveness of various therapies, identification of the severity of endothelial cell abnormalities, susceptibility to atherosclerosis, and prognosis of the patient's outcome, including risk of a future vascular event.

An assay consisting of a combination of the biomarkers referenced in the instant invention may be constructed to provide relevant information related to differential diagnosis. Such a panel may be constructed using 1, 2, 3, 4, 5, 6, 7, 8, 9, 10, 15, 20, or more individual markers. The analysis of a single biomarker or subsets of biomarkers comprising a larger panel of biomarkers could be carried out using methods described within the instant invention to optimize clinical sensitivity or specificity in various clinical settings.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" and capillary devices.

Biomarkers of the present invention serve an important role in the early detection and monitoring of endothelial cell abnormalities associated with vascular disorders (e.g., atherosclerosis). Biomarkers are typically substances found in a bodily sample that can be measured. The measured amount can correlate with underlying disorder or disease pathophysiology (e.g., presence or absence of endothelial cell abnormalities) and probability of developing a vascular disorder in the future. In patients receiving treatment for their condition, the measured amount will also correlate with responsiveness to therapy.

In some embodiments, the biomarker is measured by a method selected from the group consisting of immunohistochemistry, immunocytochemistry, immunofluorescence, immunoprecipitation, western blotting, and ELISA.

Clinical Assay Performance

The methods of the present invention for detecting endothelial cell abnormalities may be used in clinical assays to diagnose or prognose a vascular disorder in a subject, identify a subject at risk of a vascular disorder (e.g., atherosclerosis), and/or for prescribing a therapeutic regimen or predicting benefit from therapy in a subject having a vascular disorder. Clinical assay performance can be assessed by determining the assay's sensitivity, specificity, area under the ROC curve (AUC), accuracy, positive predictive value (PPV), and negative predictive value (NPV). Disclosed herein are assays for diagnosing or prognosing a vascular disorder in a subject, identifying a subject at risk of a vascular disorder, or for prescribing a therapeutic regimen or predicting benefit from therapy in a subject having a vascular disorder.

The clinical performance of the assay may be based on sensitivity. The sensitivity of an assay of the present invention may be at least about 40%, 45%, 50%, 55%, 60%, 65%, 70%, 75%, 80%, 85%, 90%, 95%, 99%, or 100%. The clinical performance of the assay may be based on specificity. The specificity of an assay of the present invention may be at least about 40%, 45%, 50%, 55%, 60%, 65%, 70%, 75%, 80%, 85%, 90%, 95%, 99%, or 100%. The clinical performance of the assay may be based on area under the ROC curve (AUC). The AUC of an assay of the present invention may be at least about 0.5, 0.55, 0.6, 0.65, 0.7, 0.75, 0.8, 0.85, 0.9, or 0.95. The clinical performance of the assay may be based on accuracy. The accuracy of an assay of the present invention may be at least about 40%, 45%, 50%, 55%, 60%, 65%, 70%, 75%, 80%, 85%, 90%, 95%, 99%, or 100%.

Compositions

Compositions useful in the methods of the present invention include compositions that specifically recognize one or more biomarkers associated with endothelial cell abnormalities, including CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein, or any combination thereof. In some embodiments, the composition enhances the activity of at least one biomarker. In other embodiments, the composition decreases the activity of at least one biomarker. In yet other embodiments, the composition comprises a peptide, a nucleic acid, an antibody, or a small molecule.

In certain embodiments, the present invention relates to compositions that specifically detect a biomarker associated with endothelial cell abnormalities. As detailed elsewhere herein, the present invention is based upon the finding that endothelial-derived exosomal CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein proteins are specific biomarkers for endothelial cell abnormalities, which may be associated with atherosclerosis and other vascular disorders. In one embodiment, the compositions of the invention specifically bind to and detect one or more of the biomarkers CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOS-TRIN, LOXL2, LAT-1, and p-glycoprotein, or any combination thereof. The composition of the present invention can comprise an antibody, a peptide, a small molecule, a nucleic acid, and the like.

In some embodiments, the composition comprises an antibody, wherein the antibody specifically binds to a biomarker or endothelial cell-derived exosomes. The term "antibody" as used herein and further discussed below is intended to include fragments thereof which are also specifically reactive with a biomarker or vesicle (e.g., exosome). Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. Antigen-binding portions may also be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), single domain antibodies, bispecific antibodies, chimeric antibodies, humanized antibodies, diabodies and polypeptides that contain at least a portion of an immunoglobulin that is sufficient to confer specific antigen binding to the polypeptide. In certain embodiments, the antibody further comprises a label attached thereto and able to be detected (e.g., the label can be a radioisotope, fluorescent compound, enzyme or enzyme co-factor).

In certain embodiments, an antibody of the invention is a monoclonal antibody, and in certain embodiments, the invention makes available methods for generating novel antibodies that specifically bind the biomarker or the exosome of the invention. For example, a method for generating a monoclonal antibody that specifically binds a biomarker or exosome, may comprise administering to a mouse an amount of an immunogenic composition comprising the biomarker or exosome, or fragment thereof, effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monocolonal antibody that binds specifically to the biomarker or exosome. Once obtained, a hybridoma can be propagated in a cell culture, optionally in culture conditions where the hybridoma-derived cells produce the monoclonal antibody that binds specifically to the biomarker or exosome. The monoclonal antibody may be purified from the cell culture.

The term "specifically reactive with" or "specifically binds" as used in reference to an antibody is intended to mean, as is generally understood in the art, that the antibody is sufficiently selective between the antigen of interest (e.g., a biomarker or exosome) and other antigens that are not of interest. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

Antibodies can be generated to bind specifically to an epitope of an endothelial cell-derived exosome or a biomarker of the present invention, including, for example, endothelial cell-derived exosome surface markers, such as CD105, CD31, and CD146.

In addition, the techniques used to screen antibodies in order to identify a desirable antibody may influence the properties of the antibody obtained. A variety of different techniques are available for testing interaction between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), western blots, immunoprecipitation assays, immunocytochemistry, and immunohistochemistry.

In some embodiments, the present invention relates to compositions used for treating or preventing a vascular disorder. As detailed elsewhere herein, endothelial cell abnormalities are implicated in the pathology of a variety of vascular disorders, including cardiovascular and cerebrovascular diseases (e.g., atherosclerosis). Therefore, in one embodiment, the present invention provides compositions that inhibit endothelial cell abnormalities. Compositions useful for preventing and/or reducing endothelial cell abnormalities may include proteins, peptides, nucleic acids, small molecules, and the like.

Methods of Treatment

The present invention provides methods of treating a vascular disorder associated with endothelial cell abnormalities in a subject, comprising administering to the subject an effective amount of a composition, wherein the composition inhibits endothelial cell abnormalities.

Furthermore, the methods of the invention can be used for monitoring the efficacy of therapy in a patient. The method comprises: analyzing the levels of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein for endothelial cell-derived exosomes from biological samples from the patient before and after the patient undergoes the therapy, in conjunction with respective reference levels for the biomarkers. Increasing levels of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein exosomal biomarkers correlate with increased endothelial cell abnormalities and indicate that the patient is worsening or not responding to the therapy, and decreasing levels of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein exosomal biomarkers correlate with reduced endothelial cell abnormalities and indicate that the condition of the patient is improving (e.g., lower risk of atherosclerosis, thrombosis, embolism, or stroke).

In some embodiments, the methods of the invention provide a method for treating a vascular disorder the method comprising the steps of: obtaining a biological sample from a subject suspected of having a vascular disorder, wherein the sample comprises endothelial cell-derived exosomes; measuring the level of one or more biomarkers selected from the group consisting of CD81, VCAM-1, eNOS, vWF, PDGF, GPVI, YAP, TAZ, p-selectin, e-selectin, ACE/CD143, C1qR1/CD93, VE-Cadherin, CC Chemokine Receptor D6, Tie-2, TNF RI/TNFRSF1A, TNF RII/TNFRSF1B, TRA-1-85/CD147, TRAIL R1/TNFRSF10A, TRAIL R2/TNFRSF10B, VCAM-1/CD106, VE-Statin, VEGF R1/Flt-1, VEGF R2/KDR/Flk-1, VEGF R3/Flt-4, SLAM/CD150, Stabilin-1, Stabilin-2, TEM7/PLXDC1, TEM8/ANTXR1, Thrombomodulin/BDCA-3, THSD1, THSD7A, GLUT-1, CD98/LAT1, NOSTRIN, LOXL2, LAT-1, and p-glycoprotein from the biological sample, wherein an altered level of the one or more biomarkers in the sample relative to the level in a control sample is indicative of a need for treatment; and administering an effective amount of an agent to the subject thereby treating the vascular disorder in the subject.

Kits

Another aspect of the invention encompasses kits for detecting or monitoring endothelial cell abnormalities in a subject. A variety of kits having different components are contemplated by the current invention. Generally speaking, the kit will include the means for quantifying one or more biomarkers in a subject. In another embodiment, the kit will include means for collecting a biological sample, means for quantifying one or more biomarkers in the biological sample, and instructions for use of the kit contents. In certain embodiments, the kit comprises a means for enriching or isolating endothelial cell-derived exosomes in a biological sample. In further aspects, the means for enriching or isolating endothelial cell-derived exosomes comprises reagents necessary to enrich or isolate endothelial cell-derived exosomes from a biological sample. In certain aspects, the kit comprises a means for quantifying the amount of a biomarker. In further aspects, the means for quantifying the amount of a biomarker comprises reagents necessary to detect the amount of a biomarker.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications are intended to fall within the scope of the appended claims.

Example 1: Biomarker Detection and Levels in Endothelial-Derived Exosomes from Patients with Cerebrovascular Disease Biomarkers were detected and measured in endothelial-derived exosomes from patients with cerebrovascular disease as follows. Blood samples were obtained from eighteen patients with definite neurologically-relevant cerebrovascular disease (CeVD) and eighteen control subjects. Each patient had CeVD proven by MRI and 14 had experienced an ischemic cerebrovascular event with tissue damage in the 10 years prior to donating blood. Strokes had occurred one year (1 patient), two (2), three (2), four (1), five (1), six (2), eight (1), nine (2) and ten years (2 patients) prior to obtaining the study blood sample. All patients had clinical evidence of continued evolution of CeVD. Each of the eighteen control subjects matched a patient by age and gender, and donated blood concurrently with patients.

One investigator supervised harvesting and storage of all plasmas by the same methods, and processed all plasmas by the same procedures. Plasmas were analyzed without knowledge of the clinical data.

Six ml of venous blood were drawn into a 10 ml plastic syringe and added to a 6 ml ACD (acid citrate dextrose) test tube (Vac Tube 0268429, Thermo-Fisher Scientific Co., Hanover Park, Ill.), incubated for 10 min at room temperature and centrifuged at 20° C. for 15 min at 600×g. Three ml of the supernatant platelet-rich plasma (PRP) were transferred to a 15 ml plastic test tube containing 3 ml of calcium- and magnesium-free Dulbecco's balanced salt solution (DBS) with 2 mM EDTA (pH 7.4) and $PGE_1$ (P5515, Sigma-Aldrich, Inc., St. Louis, Mo.) at 1 μM final concentration ($DBS^{++}$) and mixed. The diluted PRP was centrifuged at 2,200×g for 20 min at 20° C. and supernatant platelet-poor plasma (PPP) then was removed and used immediately or stored in 0.5 ml aliquots at −80° C.

Aliquots of 0.50 ml of diluted (1:1, v:v) PPP were incubated with 0.15 ml of thromboplastin-D (Fisher Scientific, Inc., Hanover Park, Ill.) followed by addition of 0.35 ml of DBS with protease inhibitor cocktail (Roche Applied Sciences, Inc., Indianapolis, Ind.) and phosphatase inhibitor cocktail (Pierce Halt, Thermo Scientific, Inc., Rockford, Ill.) as previously described (Goetzl et al. Faseb J. 2016; 30:4141-4148). After centrifugation at 3,000×g for 30 min at 4° C., supernatants were incubated with 252 μL of EXO-QUICK exosome precipitation solution (EXOQ; System Biosciences, Inc., Mountainview, Calif.), and the resultant suspensions were centrifuged at 1,500×g for 30 min at 4° C. Each pellet was re-suspended in 350 μl of distilled water with inhibitor cocktails for immunochemical enrichment of exosomes from endothelial sources (Goetzl et al. Neurology. 2015; 85:40-47).

Exosome suspensions each were incubated and mixed sequentially with 2.0 μg of mouse IgG1 anti-human CD31 (PECAM1, platelet and endothelial cell adhesion molecule 1) biotinylated antibody (clone MEM-05, ThermoFisher Scientific [Life Technologies], Carlsbad, Calif.) in 50 μL of 3% BSA for 90 min followed by incubation with 10 μL of Streptavidin-Plus ULTRALINK resin (Pierce-Thermo Scientific, Inc.) in 40 μL of 3% BSA for 60 min with continuous mixing at room temperature. After centrifugation at 600×g and removal of the supernatant, each pellet was resuspended in 100 μl of cold 0.05 M acetic acid, incubated at 4° C. for 10 min and centrifuged at 4° C. for 10 min at 4,000×g. These supernatants were transferred to new pre-chilled EPPENDORF tubes containing 265 μL of DBS, 10 μL of 1 M Tris-HCl (pH 8.0) and 25 μL of 10% BSA, and mixed. Each of these exosome suspensions was incubated and mixed sequentially with 2.0 μg of goat anti-human CD146/MCAM (cell surface glycoprotein MUC18/melanoma cell adhesion molecule) biotinylated antibody (Novus Biologicals, Littleton, Colo.) in 50 μL of 3% BSA for 90 min followed by incubation with 10 μl of Streptavidin-Plus ULTRALINK resin (Pierce-Thermo Scientific, Inc.) in 40 μL of 3% BSA for 60 min all at room temperature. After centrifugation at 600×g and removal of the supernatant, each pellet was resuspended in 100 μl of cold 0.05 M acetic acid, incubated at 4° C. for 10 min and centrifuged at 4° C. for 10 min at 4,000×g. These supernates were transferred to new pre-chilled EPPENDORF tubes containing 10 μL of 1 M Tris-HCl (pH 8.0) and 25 μL of 10% BSA, and mixed. Five % of each suspension was transferred to 300 μL EPPENDORF tubes for counting before addition of 365 μL of M-PER mammalian protein extraction reagent (Thermo Scientific, Inc.) containing the protease and phosphatase inhibitors for storage at −80° C. Platelet-derived exosomes (EDEs) were enriched immunochemically from plasmas of the same patients and control subjects as described (Goetzl et al. Faseb J. 2016; 30:2058-2063).

For counting of exosomes, each suspension was diluted 1:50 in PBS. The mean diameter (nm) and concentration (particles/ml) of exosomes in each suspension were determined using the NANOSIGHT NS500 system with a G532 nm laser module and NTA 3.1 nanoparticle tracking software (Malvern Instruments, Malvern, UK). Camera settings were: gain 366; shutter 31.48; frame rate 24.9825 fps/s; Brownian motion was captured by five repeated 20 sec video recordings.

EDE proteins were quantified by ELISA kits for human endothelial nitric oxide synthase (eNOS), glucose transporter 1 (GLUT1), lysyl-oxidase homolog-2 (LOXL2), platelet glycoprotein VI (GPVI) and the tetraspanning exosome marker CD81 (American Research Products, Inc.-Cusabio, Waltham, Mass.), angiopoietin-2 and von Willebrand factor (vWF) (Life Technologies-ThermoFisher Scientific), vascular cell adhesion molecule-1 (VCAM-1) and platelet-derived growth factor (PDGF-AB) (RayBiotech, Norcross, Ga.) according to suppliers' directions. The mean value for all determinations of CD81 in each assay group was set at 1.00 and the relative values of CD81 for each sample used to normalize their recovery.

A Shapiro-Wilks test showed that data in all sets were distributed normally. The statistical significance of differences between means for each patient group and their respective control group was determined with an unpaired Student's t-test including a Bonferroni correction (GraphPad Prism 6, La Jolla, Calif.).

The mean (±SEM) ages of the patients with atherosclerotic CeVD and controls were 75.3±2.71 years and 74.6±2.94 years, respectively, and each group had nine females and nine males. Clinically-apparent non-cerebral arterial disease was found in six of the patients (two coronary, one peripheral and three both coronary and peripheral), but none of the controls. Medication programs were heterogeneous with seven patients on low-dose aspirin and three on an oral anticoagulant. None of the controls had any evidence of atherosclerotic arterial disease. Four controls were on low-dose aspirin, but none was on an anticoagulant.

Counts of the twice immuno-enriched EDE suspensions showed mean (±SEM) values of 10.7±0.77×10$^9$/ml for controls and 6.58±0.58×10$^9$/ml for patients, that were significantly different (p=0.0004 by an unpaired t test). The mean (±SEM) diameters of the EDEs were 230±3.00 nm for the controls and 246±6.18 nm for the patients, that were not significantly different. Endothelial cell marker proteins in plasma endothelial-derived exosomes (EDEs) and platelet-derived exosomes (PDEs) isolated separately from the same controls and patients were quantified and the results are shown in Table 1 below. As for the counts, EDE levels of the exosomal marker CD81 were significantly higher for controls than patients (p=0.0064). CD81 levels in PDEs from both groups were significantly higher than those of EDEs. All other values were normalized for their levels of CD81 (see Table 1). For controls and patients, the levels of the endothelial cell protein markers VCAM-1 and eNOS were significantly more than 10-fold higher for EDEs than PDEs. As expected, levels of the platelet marker GPVI was significantly more than six-fold higher for PDEs than EDEs of controls and patients. Levels of PDGF and vWF, that are present at substantial concentrations in both platelets and endothelial cells, were several-fold higher in PDEs than EDEs of controls but nearly identical in EDEs and PDEs of patients. For VCAM-1, vWF and PDGF, EDE levels were significantly higher for patients than controls. In contrast, only levels of PDGF (p=0.001) and those of GPVI (p<0.0001) were significantly higher in PDEs of patients than controls.

Example 2: Biomarker Detection and Levels in Endothelial-Derived Exosomes from Patients with Cerebrovascular Disease and Cardiovascular Disease Various biomarkers of the present invention were detected and measured in endothelial-derived exosomes (EDE) from patients with cerebrovascular disease and cardiovascular disease as follows. Blood samples were obtained from ten patients with cerebrovascular disease (CeVD), ten patients with coronary artery disease (CoAD), 8 patients with both CeVD and CoAD, and twenty-five control subjects. Each of the twenty-five control subjects matched a patient by age and gender, and donated blood concurrently with patients.

Blood samples from the subjects were processed and endothelial-derived exosomes were isolated as described above in Example 1. EDE proteins were quantified using ELISA kits for GLUT-1, LAT-1, P-gp, VCAM-1, and NOSTRIN. The mean value for all determinations of CD81 in each assay group was set at 1.00 and the relative values of CD81 for each sample used to normalize their recovery.

A Shapiro-Wilks test showed that data in all sets were distributed normally. The statistical significance of differences between means for each patient group and their respective control group was determined with an unpaired Student's t-test including a Bonferroni correction (GraphPad Prism 6, La Jolla, Calif.).

As shown in FIGS. 2A-2E, the mean levels of all five biomarker proteins in plasma EDEs for CoAD, CeVD, and

TABLE 1

| Exosome Cellular Type | Subject Group | CD81 | VCAM-1 | eNOS | vWF | PDGF | GPVI |
|---|---|---|---|---|---|---|---|
| EDE | C | 817 ± 69.0* | 3758 ± 678* | 25.8 ± 2.71† | 11882 ± 2868† | 557 ± 114† | 204 ± 48.6† |
| PDE | C | 2587 ± 394 | 323 ± 72.8 | 2.15 ± 0.59 | 60744 ± 9474 | 1936 ± 202 | 1329 ± 141 |
| EDE | CeVD | 512 ± 74.3† | 12626 ± 3004* | 26.4 ± 2.65† | 90680 ± 21936‡ | 3063 ± 381‡ | 398 ± 85.3† |
| PDE | CeVD | 1962 ± 192 | 306 ± 40.1 | 2.02 ± 0.38 | 93042 ± 17201 | 3043 ± 208 | 2633 ± 226 |

Each value (pg/ml or for eNOS IU/ml) is the mean ± S.E.M. for 14 of the 20 patients with cerebrovascular disease (CeVD) and their age- and gender-matched control subjects (C). All protein levels were normalized by their CD81 value. P values calculated by an unpaired t test comparing the levels for EDEs with those for PDEs are shown by the symbols:
*,<0.01;
†,<0.0001;
‡,not significant.

CD81-normalized EDE levels of proteins characteristic of endothelial cells and implicated in atherosclerosis were quantified for all patients and controls. The levels of all six proteins were significantly higher for CeVD patients than matched controls (see FIG. 1).

These results showed that EDE levels of VCAM-1, eNOS, vWF, PDGF, GLUT-1, LOXL-2, Angiopoietin-2, and GPVI are increased in subjects with cerebrovascular disease. These results demonstrated that the methods of the present invention are useful for detecting biomarkers and measuring biomarker protein levels in endothelial cell-derived exosomes. These results further demonstrated that the methods of the present invention may be used to detect endothelial cell abnormalities associated with pathogenesis of vascular diseases, including cardiovascular and cerebrovascular diseases. These results further showed that methods of the present invention are useful for prognosis, diagnosis, treating or monitoring treatment of endothelial cell abnormalities associated with vascular diseases. The results suggested that the methods of the present invention would be useful for treating vascular, cardiovascular, and cerebrovascular diseases.

both CoAD and CeVD were significantly higher than the respective means for control plasma samples. For all three CV endothelial cell-selective biomarker proteins GLUT-1, LAT-1 and P-gp, mean levels for patients with CeVD were significantly higher than those for patients with CoAD alone and there was no overlap between levels for patients with CeVD and those for control samples. In contrast, the two biomarker proteins VCAM-1 and NOSTRIN that are widely distributed in endothelial cells of all vascular beds had mean levels for patients with CeVD which were no different than those for patients with CoAD alone and there was overlap between levels for patients with CeVD and those for controls.

These results showed that EDE levels of GLUT-1, LAT-1, P-gp, VCAM-1, and NOSTRIN are increased in subjects with cardiovascular disease and cerebrovascular disease. These results demonstrated that the methods of the present invention are useful for detecting biomarkers and measuring biomarker protein levels in endothelial cell-derived exosomes. These results further demonstrated that the methods of the present invention may be used to detect endothelial cell abnormalities associated with pathogenesis of vascular diseases, including cardiovascular and cerebrovascular diseases. These results demonstrated that methods of the present invention are useful for the differential diagnosis of cerebrovascular disease, cardiovascular disease (e.g., coronary artery disease), or both cerebrovascular and cardiovascular diseases. These results further showed that methods of the present invention are useful for prognosis, diagnosis, treating or monitoring treatment of endothelial cell abnormalities associated with vascular diseases. The results suggested that the methods of the present invention would be useful for treating vascular, cardiovascular, and cerebrovascular diseases.

Example 3: NOSTRIN Detection and Levels in Endothelial-Derived Exosomes from Patients with Cerebrovascular Disease NOSTRIN was detected and measured in endothelial-derived exosomes from patients with cerebrovascular disease as follows. Blood samples were obtained from eighteen patients with cerebrovascular disease (CeVD) and eighteen control subjects.

Blood samples from the subjects were processed and endothelial-derived exosomes were isolated as described above in Example 1. NOSTRIN and eNOS protein levels were quantified using ELISA kits for NOSTRIN and eNOS. The mean value for all determinations of CD81 in each assay group was set at 1.00 and the relative values of CD81 for each sample used to normalize their recovery.

A Shapiro-Wilks test showed that data in all sets were distributed normally. The statistical significance of differences between means for each patient group and their respective control group was determined with an unpaired Student's t-test including a Bonferroni correction (GraphPad Prism 6, La Jolla, Calif.).

Figure 3A:
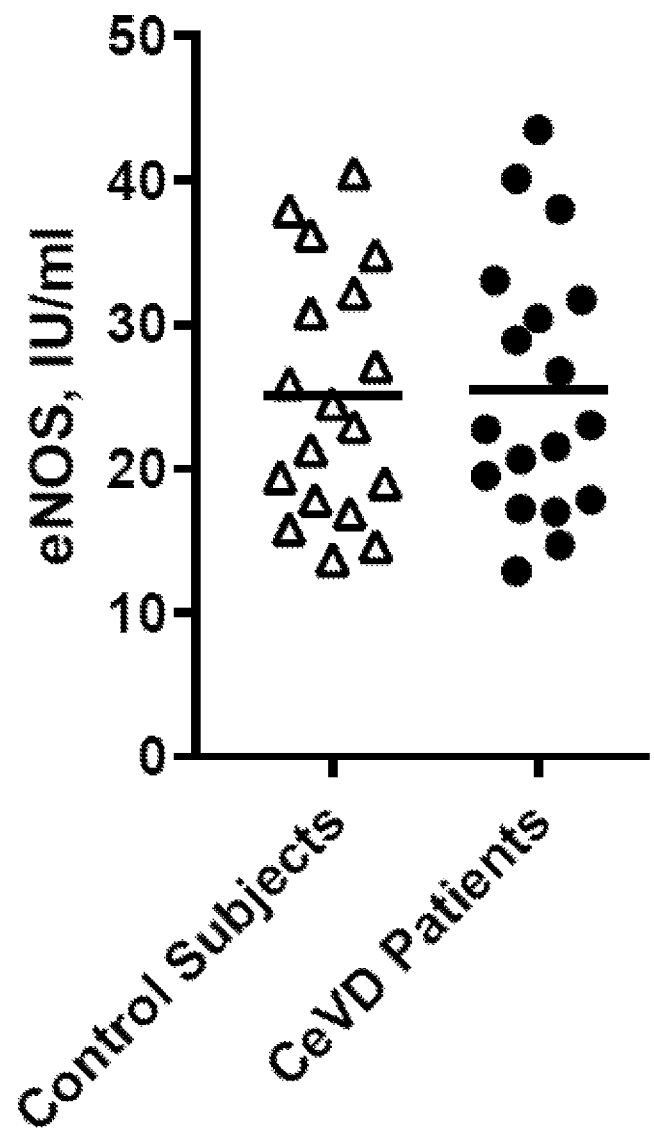
FIGS. 3A-3B set forth data showing levels of eNOS and NOSTRIN in plasma endothelial-derived exosomes (EDEs) of patients with cerebrovascular disease (CeVD) and matched controls without cerebrovascular disease. The mean for each group is depicted by the horizontal line in that cluster.
Figure 3B:
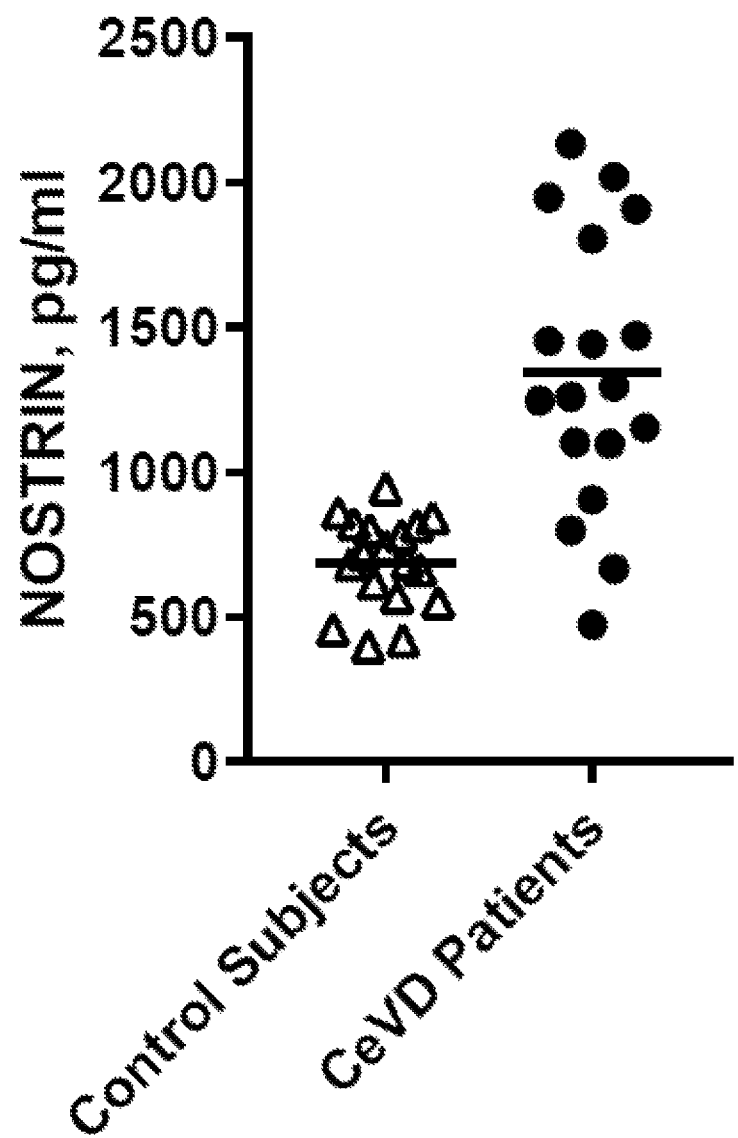

As shown in FIGS. 3A-3B, the eNOS mean±SEM values were 25.1±2.02 IU/ml for control subjects and 25.5±2.13 IU/ml for CeVD patients, and the NOSTRIN mean±SEM values were 688±37.3 pg/ml for control subjects and 1343±113 pg/ml for CeVD patients. The difference between NOSTRIN levels for the two groups is significant with $p<0.0001$ by an unpaired t test, whereas there was no significant difference between eNOS levels of the two groups.

These results showed that EDE levels of NOSTRIN are increased in subjects with cerebrovascular disease. These results demonstrated that the methods of the present invention are useful for detecting biomarkers and measuring biomarker protein levels in endothelial cell-derived exosomes. These results further demonstrated that the methods of the present invention may be used to detect endothelial cell abnormalities associated with pathogenesis of vascular diseases, including cardiovascular and cerebrovascular diseases. These results further showed that methods of the present invention are useful for prognosis, diagnosis, treating or monitoring treatment of endothelial cell abnormalities associated with vascular diseases. The results suggested that the methods of the present invention would be useful for treating vascular, cardiovascular, and cerebrovascular diseases.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method comprising: a) providing a biological sample comprising endothelial-derived exosomes from a subject; b) enriching the sample for endothelial-derived exosomes; and c) detecting the presence of one or more biomarkers selected from the group consisting of VCAM-1, eNOS, vWF, PDGF, GPVI, Angiopoietin-2 (Tie-2), VCAM-1/CD106, GLUT-1, LAT1, NOSTRIN, LOXL2, and p-glycoprotein in the exosomes in the sample, wherein the endothelial-derived exosomes are CD31+ and CD146+ and wherein the enriching endothelial cell-derived exosomes from the biological sample comprises: contacting the biological sample with an antibody under conditions wherein an endothelial cell-derived exosome present in the biological sample binds to the antibody to form an endothelial cell-derived exosome-antibody complex; and enriching the endothelial cell-derived exosome from the endothelial cell-derived exosome-antibody complex to obtain a sample containing the endothelial cell-derived exosome, wherein the purity of the endothelial cell-derived exosomes present in said sample is greater than the purity of the endothelial cell-derived exosomes present in said biological sample.

2. The methods of claim 1, wherein the biological sample is selected from the list consisting of whole blood, plasma, serum, lymph, amniotic fluid, urine, saliva, and umbilical cord blood.

3. A method comprising: a) providing a biological sample comprising endothelial-derived exosomes; b) isolating endothelial cell-derived exosomes from the biological sample; and c) detecting the presence of one or more biomarkers selected from the group consisting of VCAM-1, eNOS, vWF, PDGF, GPVI, Angiopoietin-2 (Tie-2), VCAM-1/CD106, GLUT-1, LAT1, NOSTRIN, LOXL2, and p-glycoprotein in the exosomes, wherein the endothelial-derived exosomes are CD31+ and CD146+ and wherein the isolating endothelial cell-derived exosomes from the biological sample comprises: contacting the biological sample with an antibody under conditions wherein an endothelial cell-derived exosome present in the biological sample binds to the antibody to form an endothelial cell-derived exosome-antibody complex; and isolating the endothelial cell-derived exosome from the endothelial cell-derived exosome-antibody complex to obtain a sample containing the endothelial cell-derived exosome, wherein the purity of the endothelial cell-derived exosomes present in said sample is greater than the purity of the endothelial cell-derived exosomes present in said biological sample.

4. The method of claim 3, wherein the antibody is an anti-CD105 antibody, an anti-CD31 antibody, an anti-CD81 antibody, or an anti-CD146 antibody.

5. The methods of claim 3, wherein the biological sample is selected from the list consisting of whole blood, plasma, serum, lymph, amniotic fluid, urine, saliva, and umbilical cord blood.

* * * * *